(12) United States Patent
Rubin

(10) Patent No.: US 12,023,664 B2
(45) Date of Patent: Jul. 2, 2024

(54) METHOD AND KIT FOR PRESERVATION OF ADIPOSE TISSUE GRAFTS

(71) Applicant: University of Pittsburgh—Of the Commonwealth System of Higher Education, Pittsburgh, PA (US)

(72) Inventor: J. Peter Rubin, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 389 days.

(21) Appl. No.: 16/642,585

(22) PCT Filed: Aug. 31, 2018

(86) PCT No.: PCT/US2018/049083
§ 371 (c)(1),
(2) Date: Feb. 27, 2020

(87) PCT Pub. No.: WO2019/046713
PCT Pub. Date: Mar. 7, 2019

(65) Prior Publication Data
US 2020/0346208 A1 Nov. 5, 2020

Related U.S. Application Data

(60) Provisional application No. 62/553,322, filed on Sep. 1, 2017.

(51) Int. Cl.
*B01L 3/00* (2006.01)
*B01L 7/00* (2006.01)
(Continued)

(52) U.S. Cl.
CPC ............ *B01L 3/5021* (2013.01); *C12M 33/14* (2013.01); *C12M 45/05* (2013.01); *C12M 45/22* (2013.01);
(Continued)

(58) Field of Classification Search
CPC .... B01L 3/5021; B01L 7/50; B01L 2200/026; B01L 2300/021; B01L 2300/0609;
(Continued)

(56) References Cited

U.S. PATENT DOCUMENTS 4,554,073 A * 11/1985 Schluter ............... G01N 33/491
210/450
5,744,360 A 4/1998 Hu et al.
(Continued)

FOREIGN PATENT DOCUMENTS

CA 2193945 A1 1/1996
CN 103651331 A 3/2014
(Continued)

OTHER PUBLICATIONS

Xiangdong et al. "The Search for a Useful Method for the Optimal Cryopreservation of Adipose Aspirates: Part II. In Vivo Study", Aesthetic Surgery Journal, 2010, pp. 451-456, vol. 30, No. 3.
(Continued)

*Primary Examiner* — Benjamin R Whatley
*Assistant Examiner* — Jacqueline Brazin
(74) *Attorney, Agent, or Firm* — The Webb Law Firm

(57) ABSTRACT

Methods, devices, and kits are provided for use in washing or cryopreserving live cells or tissue, such as fat graft tissue.

16 Claims, 6 Drawing Sheets

(51) Int. Cl.
  *C12M 1/00* (2006.01)
  *C12M 1/26* (2006.01)
(52) U.S. Cl.
  CPC ............ *B01L 7/50* (2013.01); *B01L 2200/026* (2013.01); *B01L 2300/021* (2013.01); *B01L 2300/0609* (2013.01); *B01L 2300/0681* (2013.01)
(58) Field of Classification Search
  CPC ...... B01L 2300/0681; B01L 2200/021; C12M 33/14; C12M 45/05; C12M 45/22; C12M 33/10; G01N 2001/4088; G01N 1/4077; G01N 1/42; G01N 1/28
  USPC .......................................................... 422/548
  See application file for complete search history.

(56) References Cited

U.S. PATENT DOCUMENTS

| | | | |
|---|---|---|---|
| 6,592,545 B1* | 7/2003 | Bellhouse | A61M 5/3015 604/141 |
| 7,989,205 B2 | 8/2011 | Moscatello | |
| 8,893,995 B2 | 11/2014 | Taghizadeh et al. | |
| 10,014,079 B2 | 7/2018 | Dudzinski et al. | |
| 10,154,664 B2 | 12/2018 | Moscatello | |
| 2004/0185554 A1* | 9/2004 | Daitch | G01N 1/2273 73/202.5 |
| 2006/0019233 A1 | 1/2006 | Yaghmour | |
| 2006/0051865 A1 | 3/2006 | Higgins et al. | |
| 2008/0176326 A1 | 7/2008 | Yaghmour | |
| 2009/0239299 A1 | 9/2009 | Buss | |
| 2009/0294385 A1* | 12/2009 | Tajima | B01L 3/0275 210/101 |
| 2012/0058027 A1* | 3/2012 | Song | B01L 3/5021 422/533 |
| 2012/0128641 A1 | 5/2012 | Austen, Jr. | |
| 2013/0123747 A1 | 5/2013 | Tremolada | |
| 2014/0024011 A1* | 1/2014 | Harris | A01N 1/0284 435/325 |
| 2016/0066563 A1 | 3/2016 | Moscatello | |
| 2016/0333305 A1 | 11/2016 | Pilkington et al. | |
| 2017/0000969 A1* | 1/2017 | Tremolada | A61M 1/88 |
| 2017/0203040 A1 | 7/2017 | Conlan et al. | |
| 2018/0187157 A1 | 7/2018 | Moeller | |

FOREIGN PATENT DOCUMENTS

| | | | | |
|---|---|---|---|---|
| JP | H114682 A | 1/1999 | | |
| JP | 2008507563 A | 3/2008 | | |
| JP | 2010150219 A | 7/2010 | | |
| JP | 2012533620 A | 12/2012 | | |
| JP | 2013526868 A | 6/2013 | | |
| WO | 2006012613 A1 | 2/2006 | | |
| WO | WO-2007102635 A1 * | 9/2007 | ............ | A61B 50/31 |
| WO | 2011011055 A2 | 1/2011 | | |
| WO | 2013070899 A1 | 5/2013 | | |
| WO | WO-2015059798 A1 * | 4/2015 | ............ | C12M 23/00 |

OTHER PUBLICATIONS

American Society of Plastic Surgeons, Plastic Surgery Statistics Report, 2016, pp. 1-25, https://www.plasticsurgery.org/news/plastic-surgery-statistics (specification).

Cui et al., "The Search for a Useful Method for the Optimal Cryopreservation of Adipose Aspirates: Part II. In Vivo Study", Aesthetic Surgery Journal, 2010, pp. 451-456, vol. 30:3.

* cited by examiner

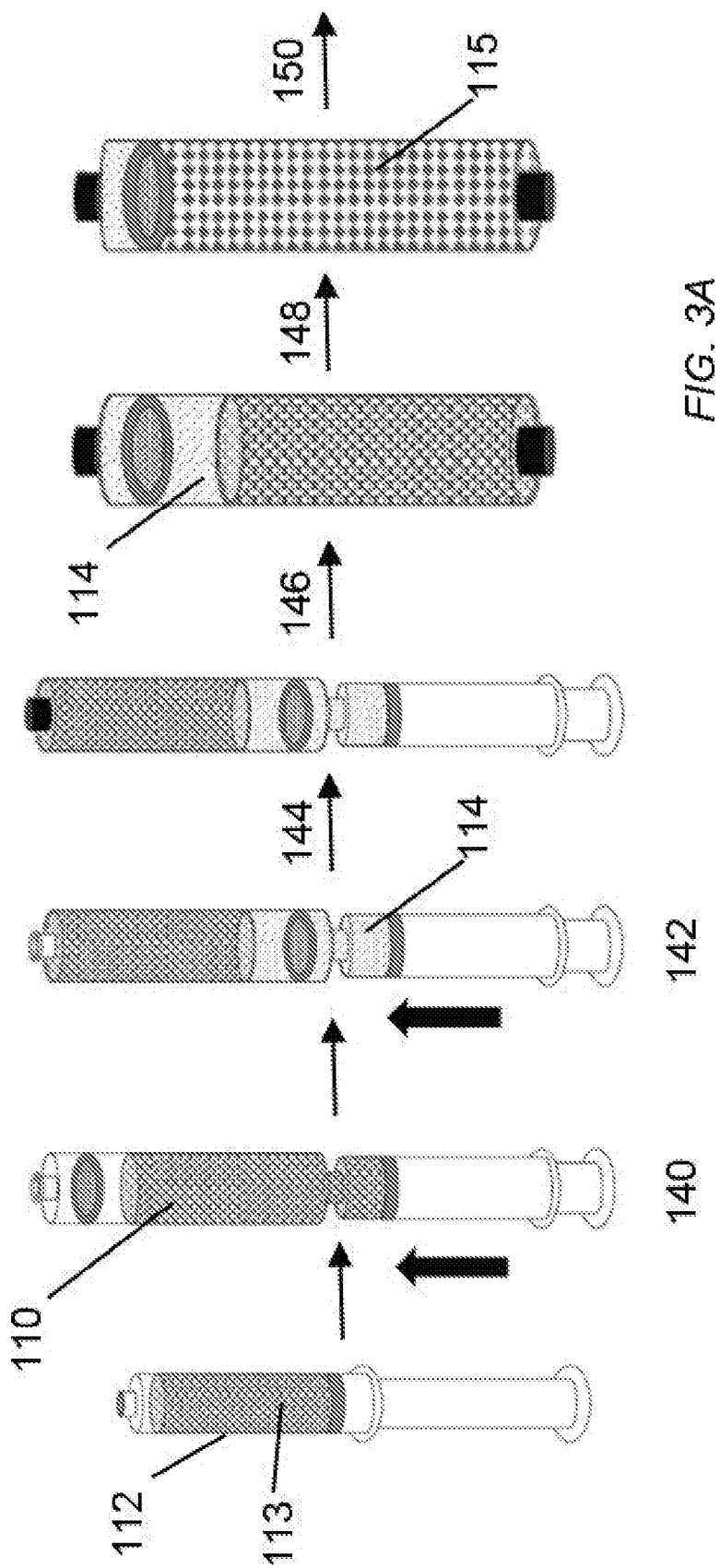

METHOD AND KIT FOR PRESERVATION OF ADIPOSE TISSUE GRAFTS

CROSS REFERENCE TO RELATED APPLICATIONS

This application is the United States national phase of International Application No. PCT/US2018/049083 filed Aug. 31, 2018, and claims the benefit of U.S. Provisional Patent Application No. 62/553,322, filed Sep. 1, 2017, each of which is incorporated herein by reference in their entirety.

STATEMENT REGARDING FEDERAL FUNDING

This invention was made with government support under Grant Number DE026915 awarded by the National Institutes of Health (NIH). The government has certain rights in the invention.

Soft tissue deformities and volume/contour deformities after craniofacial trauma, craniofacial deformities, congenital anomalies, and deformities related to cancer treatment are difficult to correct. Injectable hyaluronic acid fillers are expensive, can only fill small volumes, and degrade with time, necessitating repeat treatments. Silicone and polyethylene implant materials are permanent foreign bodies and have risk of long-term infection and displacement. Major soft tissue flap procedures are complex and have a high morbidity, and have a significant donor site deformity and risk of complications at the donor site. Autologous fat transfer is evolving as an effective means of treating soft tissue deformities with minimal donor site morbidity and fast recovery. Fat grafting also has widespread use in cosmetic surgery. Our clinical trials strongly support this therapy, especially for craniofacial fat grafting. Autologous fat grafting is a widely used procedure in plastic and reconstructive surgery, with nearly 80,000 procedures performed in the United States in 2016 by plastic surgeons (American Society of Plastic Surgeons Data, https://www.plasticsurgery.org/news/plastic-surgery-statistics).

A significant difficulty with fat grafting is that approximately 63% of the graft volume heals and persists long term, meaning that optimal results are obtained when at least two treatments are performed. Although the fat harvest is minimally invasive, there is time, cost, and recovery inherent to the procedure. Moreover, the harvest usually requires an operating room setting. Cost-effective devices and methods are required to minimalize patient discomfort and recovery time.

SUMMARY

According to one aspect of the invention, a cell or tissue isolation, purification, and storage device is provided. The device comprises: a vessel having a first end and a second end defining an internal chamber divided by a filter that retains fat cells or tissue and having a volume between the second end and the filter of at least 3 mL; a first adaptor or connector, such as a Luer lock or slip connector, at the first end of the vessel defining a first opening; and a second adaptor or connector, such as a Luer lock or slip connector, at the second end of the vessel and defining a second opening.

According to another aspect of the invention, kit is provided for use in isolating and storing cells, such as a fat graft. The kit comprises: from two to 25 cell or tissue storage devices, each storage device comprising a vessel having a first end and a second end defining an internal chamber divided by a filter that retains fat cells or tissue and having a volume between the second end and the filter of at least 3 mL; a first adaptor or connector, such as a Luer lock or slip connector, at the first end of the vessel defining a first opening; and a second adaptor or connector, such as a Luer lock or slip connector, at the second end of the vessel and defining a second opening; and at least one vessel, optionally having an adaptor or connector, such as a Luer lock or slip connector, comprising an amount of cryoprotectant able to cryopreserve at least 3 mL of cells or tissue, such as an adipose graft.

According to yet another aspect of the invention, method of preparing a fat graft is provided. The method comprises: introducing (e.g., injecting) fat tissue into the internal chamber of the device, according to any aspect above or herein, through the second opening of the device; introducing an amount of a cryoprotectant effective to cryopreserve the fat graft into the internal chamber of the device through the first opening of the device; mixing the fat tissue with the cryoprotectant; and cooling the fat graft to a temperature below 0° C.

In another aspect of the invention, a method of preparing a fat graft is provided. The method comprises: introducing (e.g., injecting) fat tissue into the internal chamber of the device, according to any aspect above or herein, through the second opening of the device; introducing an amount of a wash solution effective to wash the fat graft into the internal chamber of the device through the first opening of the device; mixing the fat tissue with the wash solution; centrifuging the device containing the fat graft with the first opening on the bottom, to separate the fat graft from the wash solution; and drawing the wash solution from the first end of the device.

In another aspect of the invention, a method of preparing a fat graft is provided, comprising: introducing (e.g., injecting) fat tissue into the internal chamber of the device, according to any aspect above or herein, through the second opening of the device; introducing an amount of a wash solution effective to wash the fat graft or an amount of a cryoprotectant effective to cryopreserve the fat graft into the internal chamber of the device through the first opening of the device; and mixing the fat tissue with the wash solution or the cryoprotectant; and either: when wash solution is introduced, centrifuging the device containing the fat graft with the first opening on the bottom, to separate the fat graft from the wash solution; and drawing the wash solution from the first end of the device, or when cryoprotectant is introduced, cooling the fat graft to a temperature below 0° C.

BRIEF DESCRIPTION OF THE DRAWINGS

FIG. 3A depicts schematically, in part, along with FIG. 3C, one aspect of a method of preserving a tissue graft, such as a fat graft as described herein.

DETAILED DESCRIPTION

Figure 1:
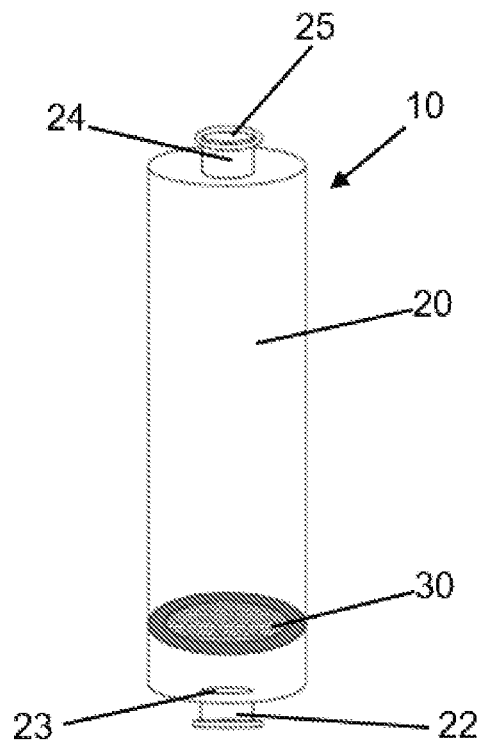
FIG. 1 depicts schematically, in partial cut-away view showing the filter, one aspect of a fat collection and storage device as described herein.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values.

As used herein, the terms "right", "left", "top", "bottom", and derivatives thereof shall relate to the invention as it is oriented in the drawing figures. However, it is to be understood that the invention can assume various alternative orientations and, accordingly, such terms are not to be considered as limiting. Also, it is to be understood that the invention can assume various alternative variations and stage sequences, except where expressly specified to the contrary. It is also to be understood that the specific devices and processes illustrated in the attached drawings, and described in the following specification, are examples. Hence, specific dimensions and other physical characteristics related to the embodiments disclosed herein are not to be considered as limiting.

The terms "distal" and "proximal" refer to directions with respect to the devices described herein, with "distal" referring to a direction away from a user of a device, such as the direction approaching the sharp needle tip of a hypodermic syringe (the distal end of the needle), and "proximal" referring to a direction toward a user of a device, such as the direction approaching the end of a plunger of a hypodermic syringe in the opposite direction from the sharp needle tip, at the proximal end of the syringe. Although "distal" and "proximal", and other spatial relationship terms, correspond to the relative position, orientation, and/or direction of element(s) of the devices described herein with respect to the end use of the device in typical use as a percutaneous device, or to other external reference points, those descriptors are provided only to describe the relative position, orientation, and/or direction of element(s) of the devices described herein with regard to the device as a whole, and to elements thereof, and, unless otherwise indicated, do not require or infer that the elements are located, positioned, oriented, or in any physical relationship with an end user at any given time. Figures are schematic in nature unless otherwise identified, and are not drawn to scale, but are drawn in a manner to best depict the relationship between the various elements of the device drawn in the figure.

As used herein, the terms "comprising," "comprise" or "comprised," and variations thereof, are meant to be open ended. The terms "a" and "an" are intended to refer to one or more.

As used herein, the "treatment" or "treating" of a condition, wound, or defect means administration to a patient by any suitable dosage regimen, procedure and/or administration route of a composition, device or structure with the object of achieving a desirable clinical/medical end-point, including repair and/or replacement of a tricuspid or mitral valve.

As used herein, the term "patient" or "subject" refers to members of the animal kingdom including but not limited to human beings and "mammal" refers to all mammals, including, but not limited to human beings.

Provided herein is a simple, cost-effective method of preserving live fat cells or tissue.

A "fluid connector" for use with syringes, cannulas, and the devices and kits described herein, can be any suitable fluid connector, also referred to as a small bore fluid fitting, e.g., as are broadly-known in the medical arts (e.g., ISO 80369). Common connectors include slip or threaded connectors such as slip or threaded Luer connectors, as are common for use with medical and laboratory equipment or instruments, such as hypodermic syringes. The connectors can be matched by color or structure to ensure proper orientation and usage of the device.

"Syringe," as used herein refers to a medical or hypodermic syringe, as are broadly-known in the medical arts, and can be manufactured from glass, plastic, ceramics, and/or any acceptable material. The structure and function of a syringe, and its components are broadly-known. A "cannula" is a hollow tube having a blunt end, while a "needle" for purposes of the devices and kits described herein, refers to a hollow tub having a sharp or pointed end for ease of piercing tissue, e.g., skin, blood vessels, or other tissue. For aspiration of fat, a cannula may be preferred so as to lessen the chance of puncture wounds. For use of a cannula, a needle, or other "sharp" device may first be used to puncture the patient's skin. Both needles and cannulas have a distal end (for insertion into a patient), comprising an opening and, in the case of needles, a sharp or pointed end, as are broadly-known. They also have a proximal end comprising a suitable fluid connector, such as a Luer connector, for attachment to a syringe. Cannulas for fat harvesting can include a closed tip, with one or more openings in the wall of the cannula, in various patterns adjacent to its distal end. Such cannulas are broadly-available, such as Tulip Cell-Friendly™ cannulas and harvesting cannulas, available from Tulip Medical Products of San Diego, California, or from MicroAire of Charlottesville, Virginia, among others.

A "cryoprotectant" is a composition that can be added to live cells and protect the cells from exposure to freezing temperatures (e.g., cryopreservation), such as a temperature below 0° C., such as −20° C. or −80° C., resulting in substantial viability of the cells after subjecting the cells to freezing temperatures. The cryoprotectant is typically non-toxic when used for preservation of cells. Suitable cryoprotectants useful for protection of human cells include: dimethyl sulfoxide (DMSO), human serum albumin, trehalose, and any effective combination of the preceding, optionally further including autologous plasma or autologous serum. Effective amounts of the cryoprotectant, such as 10% v/v DMSO, are known to those of ordinary skill, and effective or optimized amounts of cryoprotectants are readily ascertained. Likewise, slow cooling and thawing of the fat graft may be desirable in obtaining good viability of the harvested tissue. Reference is made to Example 2, below for cryopreservation of fat cells.

Fat grafting is a surgical procedure that involves aspiration of fat donor tissue from the subcutaneous tissues through a hollow bore cannula. The abdomen is a common donor site. The fat graft is injectable, making both the harvest and grafting procedure minimally invasive. The fat graft is composed of small particles of fat tissue, approximately 2-5 mm in diameter, that form a viscous injectable slurry. Saline solution containing epinephrine is infused into the donor subcutaneous tissues prior to harvest. This infusion of "wetting solution" minimizes bleeding, but also contributes an aqueous fluid component to the harvested tissue that needs to be separated before grafting. The standard technique for harvesting and grafting, called the "Coleman Technique," employs a hollow bore harvest cannula attached to a 10 cc Luer lock syringe. The surgeon introduces the cannula through a small incision and pulls back on the plunger to generate negative pressure. As the cannula is passed through the tissues, small particles of fat are pulled into the aperture of the harvesting cannula, avulsed from the surrounding tissue with cannula movement, and drawn into the syringe barrel. Because aqueous solution is mixed into the fat tissue from the wetting solution, as well as free lipids from lysed adipocytes, the fat graft material is separated from the other fractions by gentle centrifugation in a simple table-top blood centrifuge. This device is commonly adapted for fat grafting and present in most operating rooms for this purpose. The concentrated fat graft can be injected into the recipient tissues from the 10 cc syringe, or transferred to smaller syringes for more precise injection.

For injection, a hollow cannula very similar to the harvest cannula is attached to the syringe barrel. All of the common fat grafting instruments are designed to attach to Luer connectors and this fact is considered in the design of one aspect of the device described herein. Importantly, surgeons are used to performing the centrifuge step in the operating room with the fat directly in the 10 cc syringe used for harvesting. The syringe plungers are simply removed and the 10 cc syringe barrel fits into the sterilized tube of the centrifuge. This point is directly relevant to the device design, because, in aspects, the device described has the same diameter and basic length of a standard, e.g., a 10 cc syringe barrel. Therefore, the fat tissue storage device can fit into the centrifuge to facilitate post-thaw washing steps without having to change containers. The storage device is made to work seamlessly with the current equipment and methods commonly used by surgeons performing fat grafting.

A major deficiency of autologous fat grating is the fact that there is resorption of the fat graft during the initial healing, with approximately 60% of the volume of the graft remaining after healing. Therefore, multiple treatments are often necessary. Since the donor harvest procedure to obtain the fat graft is a procedure that requires an operating room setting, and special equipment to process the fat tissue, it would significantly reduce cost, risk, discomfort, and improve care if fat tissue could be stored at the time of surgery for later use. The tissue can be stored on site in small aliquots that can be injected into the site of injury in an office setting for refinement of the results. Because the tissue is stored on site, it would enable multiple treatments with minimal additional cost to the original fat harvest and original fat processing.

In aspects, a device is provided in a kit comprising a cryopreservative, and special multi-function vessels that are used for mixing the fat graft with the cryo-preservative, storage, and washing steps after thawing. In one example, the individual vessels each hold approximately 10 cc of graft material, and are stored together in a special storage container that continuously records temperature and allows individually aliquots to be removed while preserving other vessels for continued storage. The large storage container that hold the individual vessels may be included in each kit.

In aspects, the individual single use multifunction vessels have Luer lock ports so that the system can connect with standard syringes used for fat grafting. A built-in filter enables infusion and drainage of both cryoprotectant solution and wash solution without removing the fat graft material. The steps of adding the fat graft material, mixing with cryoprotectant, storing in a freezer, thawing, washing, and filtering all occur in the same vessel. This is a distinct advantage of this system. In addition to the Luer lock connectors, the device optionally can be opened at one end to allow the fat graft to be poured into another sterile container as desired, or if clogging of the Luer lock port occurs. As indicated above, in one aspect, the multi-function vessels are the same diameter as a standard 10 cc syringe and nearly the same length, enabling them to be used in the same table-top centrifuge already employed for fat grafting and commonly found in operating rooms.

Advantages of the devices, kits and methods described herein include:

Tissue grafts can be stored on site, with very simple preparation and at a low cost;

Aliquots of fat graft can be removed from storage while remaining aliquots are left intact for future use;

All mixing, storage, and washing of the fat grafts occurs in the same single use multi-function vessel;

The multi-function vessel is designed to work seamlessly with commonly used fat graft equipment and standard syringes; and Use of the equipment will be very intuitive for any surgeons who perform fat grafting.

Thus, devices, kits and methods are provided herein for use in harvesting and storage of fat cells and tissue. In one aspect, a storage vessel is provided. Referring to FIG. 1, a cylindrical device 10 is depicted. The device 10 and its components are manufactured from suitable materials to withstand cell and tissue cryopreservation conditions, ranging from physiological temperature (37° C.) to storage under cryopreservation conditions, e.g., to −20° C., −80° C., or −196° C. (liquid nitrogen), such as suitable polycarbonates or polypropylenes, as are known in the cryopreservation and centrifugation arts, and suitable metallic screens or filters. In aspects, the device 10 is dimensioned to fit into a typical clinical laboratory centrifuge able to centrifuge devices (e.g. tubes, bottles, or syringes), that is, in one aspect, it is dimensioned, e.g., as a typical 5 mL to 100 mL, e.g., 5 mL, 10 mL, 15 mL, 20 mL, 30 mL, or 60 mL medical syringe, a typical 5 mL to 50 mL, centrifuge tube (e.g., conical centrifuge tube), or a typical blood collection tube, that is, having an outside diameter of from 5 mm to 25 mm, e.g., from 12 mm to 25 mm, and a length (barrel length, excluding connectors) of from 70 mm to 110 mm. For example, a storage vessel for use with a 10 mL syringe may have an outside diameter ranging from 16.5 mm to 18 mm, and a barrel length ranging from 80 mm to 90 mm. In one example, the ratio of the length of the barrel to the outside diameter of the barrel is at least 4:1, e.g., from 4:1 to 6:1. In aspects, the device 10 is custom sized, but fits into a rotor, either with a custom or standard rotor or a custom or standard rotor insert, of a centrifuge, and its volume may range from 3 mL to 100 mL, or greater. A "centrifuge able to centrifuge tubes, bottles, or syringes having a volume within the range of from 1 mL to 4 L" is a centrifuge that is commonly found in operating rooms, clinical laboratories, outpatient facilities, and physicians offices, or a custom centrifuge and is capable of centrifuging devices having a volume falling within the range of from 1 mL to 4 L, such as a 10 mL tube, but does not necessarily have the capacity to centrifuge all volumes within that range. For example "a centrifuge able to centrifuge tubes, bottles, or syringes having a volume within the range of from 1 mL to 4 L" may only be able to centrifuge tubes in the range of from 3 mL to 30 mL, or from 10 mL to 60 mL, but not outside that range.

Referring again to FIG. 1, the device 10 comprises a vessel, depicted as a cylindrical barrel 20 that has a wall and an internal chamber (that is, an internal void, or a lumen). The vessel is depicted as a barrel, but may have any suitable shape, though a cylindrical barrel shape may be preferred. The device 10 also comprises a first end having a first fluid connector 22 comprising an opening 23 extending through the first fluid connector 22 and into the lumen of the barrel 20, and a second end having a second fluid connector 24 comprising an opening 25 extending through the second fluid connector 24 and into to the lumen of the barrel 20. The first fluid connector 22, the barrel 20, and the second fluid connector 24 together form a closed fluid path between the opening of the first fluid connector 22 and the opening of the second fluid connector 24. A filter 30 is placed within the barrel 20, adjacent to the first fluid connector 22, and is configured to filter liquids passing through the closed fluid path between the opening of the first fluid connector 22 and the opening of the second fluid connector 24. That is, the filter 30 spans a complete cross-section of the lumen of the barrel, so that fluid passing along the closed fluid path between the opening of the first fluid connector 22 and the opening of the second fluid connector 24, passes through the filter 30. The filter 30 can be manufactured from any suitable material able to withstand cryopreservation temperatures, e.g., ranging from −196° C. to 37° C., such as a metallic mesh, e.g., a stainless steel mesh. The filter may be any suitable pore size or mesh size, such as ranging from 50 microns (μ) to 250μ filters, or other porous barrier that serves a filtering purpose, such that a majority of the adipose tissue is retained by the filter in use. The barrel 20 has an internal volume between its second end and the filter 30 ranging from 3 mL to 100 mL, e.g., approximately 5 mL, 10 mL, 15 mL, 20 mL, 25 mL, 30 mL, 50 mL, 60 mL, or 100 mL, and increments therebetween, such as, in one non-limiting example from 9 mL to 15 mL to accommodate a tissue volume obtained using a 10 cc syringe. The device 10 optionally comprises live cells or tissue, such as live fat cells or tissue, e.g., a fat graft, such as a human fat graft, within the internal chamber of the barrel 20.

The device is designed and manufactured to withstand a G-force (a multiple of 1 g, the gravitational force at the earth's surface) of at least 500 g, e.g., at least 1000 g, 1200 g, or 1500 g, so as to withstand centrifugation conditions typical for washing and pelleting of viable fat grafts. There are a variety of common centrifugation conditions and protocols used in preparation of fat grafts, leading to viable cells, the G-force typically ranging between 400 g and 1500 g, with typical spin durations of from 1 to 5 minutes, e.g., as shown below, 1200 g for three minutes.

Figure 2:
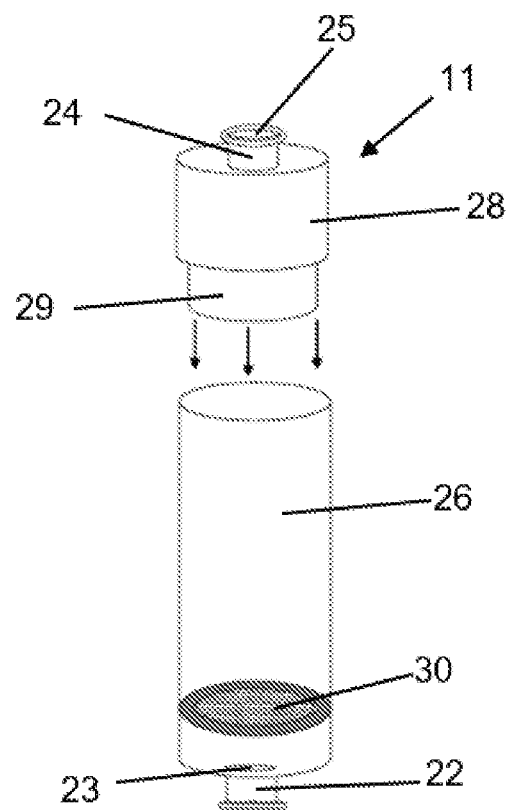
FIG. 2 depicts schematically, in partial cut-away view showing the filter, one aspect of a fat collection and storage device as described herein.

FIG. 2 depicts a second aspect of the device 11, and is essentially identical to the device 10 depicted in FIG. 1, but having a separable barrel that separates into a first barrel portion 26, and a second barrel portion 28, including a slip fitting 29. The purpose of the ability to separate the barrel portions 26 and 28 is to be able to open the barrel of the device 11 to dump the contents should the device become clogged. The device 11, comprises a first end having a first fluid connector 22 comprising an opening 23 extending through the first fluid connector 22 and into the lumen of the barrel 20, and a second end having a second fluid connector 24 comprising an opening 25 extending through the second fluid connector 24 and into to the lumen of the barrel formed by the first barrel portion 26 and the second barrel portion 28. The slip fitting 29 is configured to engage an inner surface of the first barrel portion to effectively seal the barrel and to prevent separation of the barrel portions 26 and 28, in use. Alternatively, to prevent separation of the barrel portions 26 and 28 in use, the fitting 29 may include suitable structural elements such a mating ridge on the fitting and a valley on the inside surface of the first barrel portion 26 such that the barrel portions 26 and 28 snap together. In another aspect, the fitting 29 is threaded, and the inside surface of the first barrel portion 26 is threaded or tapped, such that the barrel portions screw together and can be twisted relative to each other to separate the first barrel portion 26 from the second barrel portion 28. The fitting 29, is shown as integral to the second barrel portion 26, and alternatively, can be reversed, that is, it is integral to the first barrel portion 29.

Figure 3B:
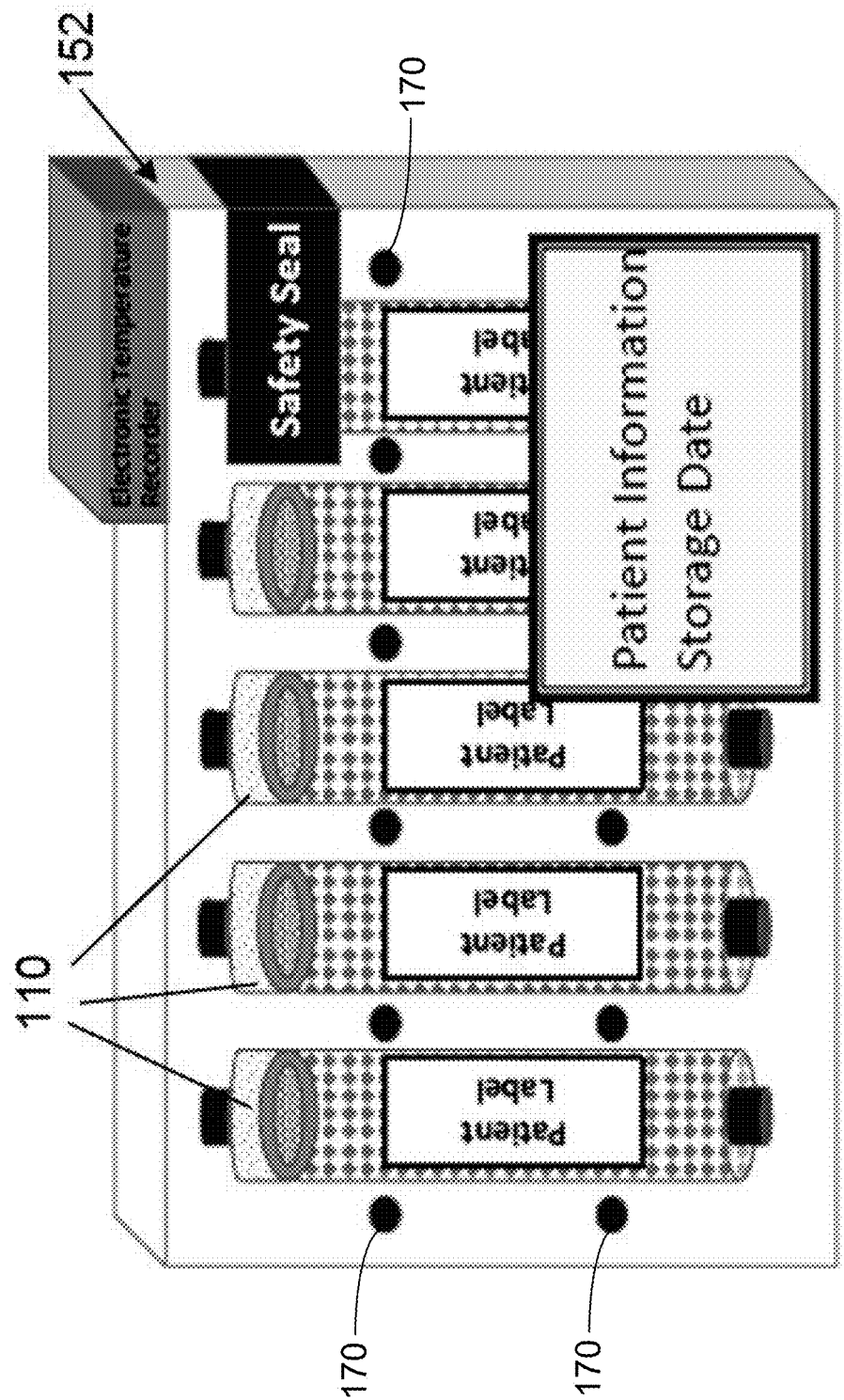
FIG. 3B depicts schematically one aspect of a storage device for use in the methods and kits described herein.
Figure 3C:
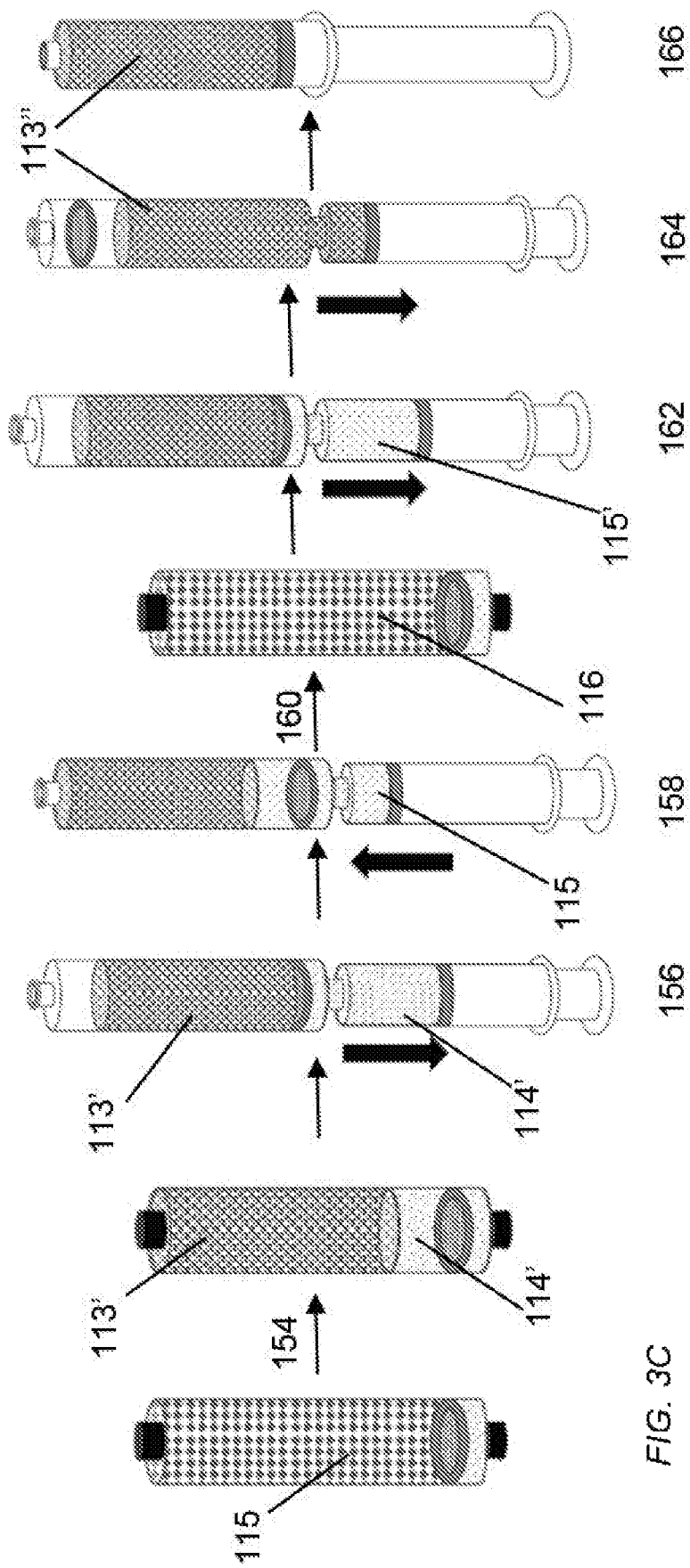
FIG. 3C depicts schematically, in part, along with FIG. 3A, one aspect of a method of preserving a tissue graft, such as a fat graft as described herein.

A method for processing and storing, e.g., cryopreserving, live fat cells or tissue (a fat graft) is provided, utilizing a storage vessel as described herein and exemplified by the device 10 of FIG. 1. FIGS. 3A-3C depict the method and elements of a kit useful for storage, e.g., cryopreservation, of fat grafts. Referring to FIG. 3a, a fat graft 113, that is, freshly aspirated fat tissue and fat cells, are drawn into a syringe 112. The fat graft 113 is injected 140 from the syringe into the second end of a device 110 (the end opposite the filter), e.g., essentially the device 10, as shown in FIG. 1, and referring to the elements as identified with respect to the device 10 of FIG. 1. The vessel is detached from the syringe 112, and cryoprotectant 114 is injected 142 into the first end of the device 110 (the end having the filter). The second end of the device 110 is capped 144, and then the first end of the device 110 is capped 146. The device 110 is then shaken to produce a mixture of the fat graft and the cryoprotectant 115. The process is repeated as many times as desired, collecting, e.g., from one to 25 tubes of fat (fat graft) from the patient and mixing the fat graft with cryoprotectant. The fat graft is then stored 150 at a temperature below 0° C., e.g., at −20° C., −80° C., or in liquid nitrogen. As used herein, "mixing" may be by any method, including shaking, inverting, placing in a shaking water bath, gently vortexing in a vortex mixture, or any suitable method that does not substantially affect viability of cells in the device.

FIG. 3B depicts an exemplary fat storage container 152 that can be distributed as part of a kit for preserving fat grafts. The container 152, as shown contains five filled storage devices 110 containing fat graft mixed with cryoprotectant. Depicted are a container 152, storage vessels with individual patient labels, including indicia relating to the patient, the container 152 also includes a safety seal, and an external label comprising indicia including patient information and storage date of the fat grafts. A temperature recorder (e.g., an electronic temperature recorder or temperature logger, as is broadly-known) is also included to track temperature variations of the fat grafts. The container can have any shape and size adequate to hold any suitable number of storage devices 110, and is manufactured from any suitable material able to withstand the temperature variations associated with the storage of the fat grafts.

Referring now to FIG. 3C, for use of the fat grafts, e.g., as a tissue filler, the storage vessel containing the mixture 115 of the fat graft and the cryoprotectant is thawed under appropriate conditions, such as on ice, or in a refrigerator, e.g., at 4° C., and is centrifuged 154 within the vessel to separate the fat graft 113' from the cryoprotectant 114', and the cryoprotectant 114' is then drawn 156 from the first end of the vessel. For purposes herein, the fat grafts are centrifuged at any suitable speed (RPM) for any suitable time to generate a suitable G-force for a suitable amount of time to effectively separate the fat graft from most of the liquid the fat graft is dispersed in (e.g., cryoprotectant or wash solutions), while retaining, optimizing, or maximizing graft viability. The vessels are centrifuged with the first end down because the adipose tissue will float on the cryoprotectant and wash solutions.

Wash solution 115, such as saline, water, phosphate buffered saline, serum-free medium, or any suitable wash solution, is introduced 158 into the first end of the vessel, which is capped and shaken 160 to produce a mixture 116 of wash solution and the fat graft. The vessel is centrifuged, as described above (not shown) to separate the wash solution 115' from the cells, and the wash solution 115' is drawn 162 from the vessel. The washing steps, 158, 160, and 162 are repeated as many times as needed to remove cryoprotectant, free lipids, and cell debris, for example, from two to six times, e.g., three times. After centrifugation, free lipids, if any, will be on top of the fat graft. The free lipids can be decanted. The vessel is flipped, and the washed fat graft 113' is drawn 164 from the vessel into a syringe, and is ready to be injected into a patient. Optionally free lipids are removed from the fat graft after removal of the wash solution 115' prior to transfer of the fat graft 113" to a syringe 164 and 166 for delivery to a patient.

Although centrifugation is particularly effective and rapid, the cells or tissue can be separated from liquids using any useful method. For example and without limitation, cell or tissue material mixed with the cryoprotectant or the wash solution can be allowed to separate without the use of a centrifuge, for example and without limitation, by placing and holding the device in a suitable rack for a sufficient time for the cell or tissue layer to separate from the liquid layer, and, depending on the location of the layer or layers of separated liquid, the liquid is then drawn or decanted from the device. Where the cells or tissue are a fat graft, the fat graft typically will have a lower specific gravity than the cryoprotectant or wash solution, in which case, once separated, the higher-density liquid is drawn from the first opening of the device. Cell-free lipids, having a lower specific gravity than the fat graft, can be decanted from the second opening of the device.

Prior to mixing the fat graft with the cryoprotectant 142, after injection of the fat graft into the device 110, the fat graft can be washed with a suitable wash solution, such as PBS or saline, as described above (156, 158, 160, 162), and free lipids can be removed, e.g., decanted after centrifugation. After thawing and washing, the fat graft can be further processed prior to use, such as by treating the graft with a collagenase, filtering to remove architectural fragments, and, optionally centrifugation to separate adipocytes from other cellular elements, including the stromal vascular fraction (SVF), comprising progenitor cells, e.g., adipose-derived stem cells (ASCs), e.g., by adherence of cells of the SVF to plastic.

In one aspect, a kit is provided for use in preserving grafts, such as fat grafts. The kit comprises suitable packaging for the elements of the kit, including boxes, molded containers or inserts 170 (shown in FIG. 3B), suitable indicia identifying the contents and outlining the method of use of the elements of the kit, as described in the method described above, and elsewhere herein. At a minimum, the kit comprises two or more storage vessels as described herein, e.g., as described in reference to FIG. 1 or FIG. 2. The kit also optionally comprises one or more vessels comprising a cryoprotectant as described herein, in an amount effective to cryoprotect a volume of graft, e.g., a fat graft, that can be drawn into the vessels of the kit. For example, for two 10 mL storage vessels, for use with a fat graft drawn into a 10 mL syringe, an amount of cryoprotectant is provided that would be effective in cryoprotecting 20 mL of fat graft material. As described above, any suitable cryoprotectant may be contained in the vessel, such as DMSO, human serum albumin, or trehalose, or an effective combination of any of the preceding. The cryoprotectant can be contained in one multi-use vessel, or in individual, single-use vessels that contain only enough cryoprotectant to treat an aspirated tissue in a single vessel. The kit also may comprise a vessel comprising a suitable wash solution in an amount appropriate for the number and size of the vessels of the kit. The vessel(s) containing the cryoprotectant or the wash solution optionally comprise a suitable connector, such as a Luer connector, for use with a syringe. The kit also optionally comprises one or more sterile syringes for obtaining the fat sample from a patient or processing the graft as described herein. A fat harvesting cannula also may be included in the kit. In addition, a storage container may be included in the kit, e.g., as shown and described in the context of FIG. 3B, and include, optionally, one or more of the following: labels for the storage vessels, label(s) for the storage container, a temperature logger, or safety seals to indicate tampering with the contents of the container. In one example, the kit comprises, in suitable packaging: five, 10, 15, 20, or 25 storage vessels, one or more vessel comprising a cryoprotectant, one or more vessels comprising a wash solution, and a storage container including, optionally, a temperature logger.

Example 1

To determine if the device described herein could withstand processing, and effectively separate fat from liquids, devices and methods as depicted in FIGS. 1, 3A, and 3C, were used to process discarded fresh human fat graft tissue collected from surgery, using 10 mL syringes, and a storage vessel essentially as depicted in FIG. 1, prepared from distal ends of two 10 mL syringes solvent welded together, with a 100μ stainless steel screen placed in the first end of the device as shown. Saline (0.9% normal saline) was used both in place of a cryoprotectant, and as a wash solution. The fat graft was centrifuged at 1200 g for 3 minutes throughout the protocol. After the final wash, excess lipids were decanted prior to drawing the fat graft into a syringe for transfer to a patient.

Example 2

Tissue Sample
Abdominal liposuction was performed from a 51-year-old female donor at the Plastic Surgery Department, University of Pittsburgh. The study was approved by the Institutional Review Board.
Cryopreserving Solution
Dimethyl sulfoxide, DMSO (Sigma) at a concentration of 5% and 10% (V/V) in PBS was used as an intracellular cryoprotectant. To achieve extracellular cryopreservation 2% human albumin (Invitrogen) alone or in combination with 0.25M Trehalose (Sigma) was employed. Following 4 combinations of cryoprotectant solutions were compared with fresh non-cryopreserved lipoaspirates.
1—10% DMSO+2% Albumin
2—10% DMSO+2% Albumin+0.25M Trehalose 3—5% DMSO+Albumin 4—5% DMSO+Albumin+0.25M Trehalose Freezing and Thawing Procedure Two different freezing conditions were used to cryopreserve lipoaspirate with an object to avoid intracellular ice crystal formation: (1) Controlled freezing to −80° C. at a rate of 1° C. decrease per minute; and (2) Freezing in −80° C. freezer in Styrofoam box. Lipoaspirates were washed twice with phosphate buffer saline, PBS (Dulbecco) by centrifuging at 500 g for 5 minutes. Upper oil layer and lower liquid layer is removed. Following washing, 10 ml lipoaspirate was added to a 50 ml Falcon tube and equal volume of ice-cooled cryopreserving agent was added. Controlled freeze samples were transferred to −80° C. freezer. Samples were thawed after 48 hours in a 37° C. water bath. Thawed tissue samples were washed twice with PBS to remove the cryopreserving agent.

Lipoaspirate Digestion

Fresh and thawed lipoaspirates were digested using Collagenase enzyme. Briefly, 10 ml lipoaspirates were incubated in 0.8 mg/ml type II collagenase (Worthington, NJ)/3% BSA/HBSS (Sigma) for 75 minutes in a shaking water bath at 37° C. Digested solution was passed through sterile gauze to remove the architectural fragments and centrifuged at 200 g for 5 min. Upper adipocyte layer was collected in separate tube and the stromal vascular fraction pellet was treated with ACK red blood cells lysis buffer, passed through 70 μm cell strainer, centrifuged (200 g, 5 min) and resuspended in DMEM, 10% FBS medium.

Cell Viability Analyses

The viability of adipocytes and SVF cells was analyzed using Countess cell counter (Invitrogen) following manufacturer's protocol.

Cell Culture

Stromal vesicular fraction cells were seeded at a rate of 10000 cell/cm$^2$ in 25 cm$^2$ flasks in DMEM/10% FCS/Gentamicin medium. Cells were incubated at 37° C. in the presence of 5% $CO_2$. Medium was changed every 2 days and cells were counted after 8 days.

Histology Study

Lipoaspirates were fixed in 10% buffered formalin saline (Fisher Scientific) for 48 hours. Fixed tissue was embedded in paraffin and cut to obtain 3-5 μm sections. Hematoxylin and eosin staining was performed to visualize the architecture.

Example 3 Cryopreservative Study

Figure 4A:
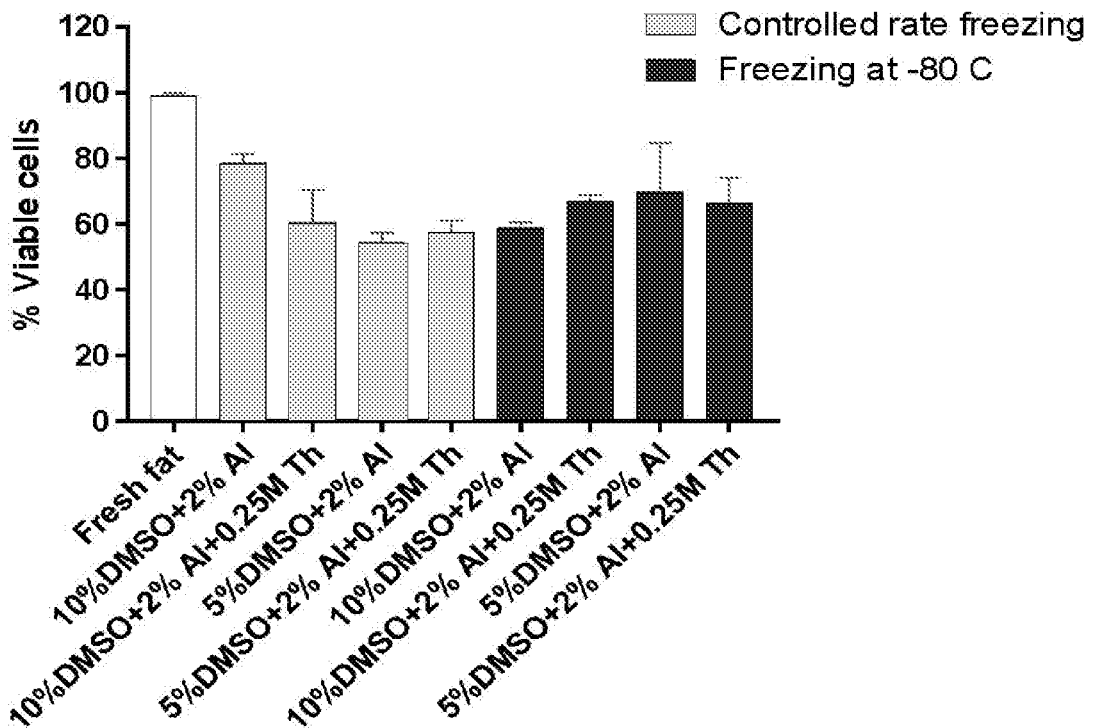
FIGS. 4A and 4B show results of analysis of ASCs (adipose-derived stem cells, FIG. 4A) and adipocytes (FIG. 4B) for viability using trypan blue stain, as described in Example 3.
Figure 4B:
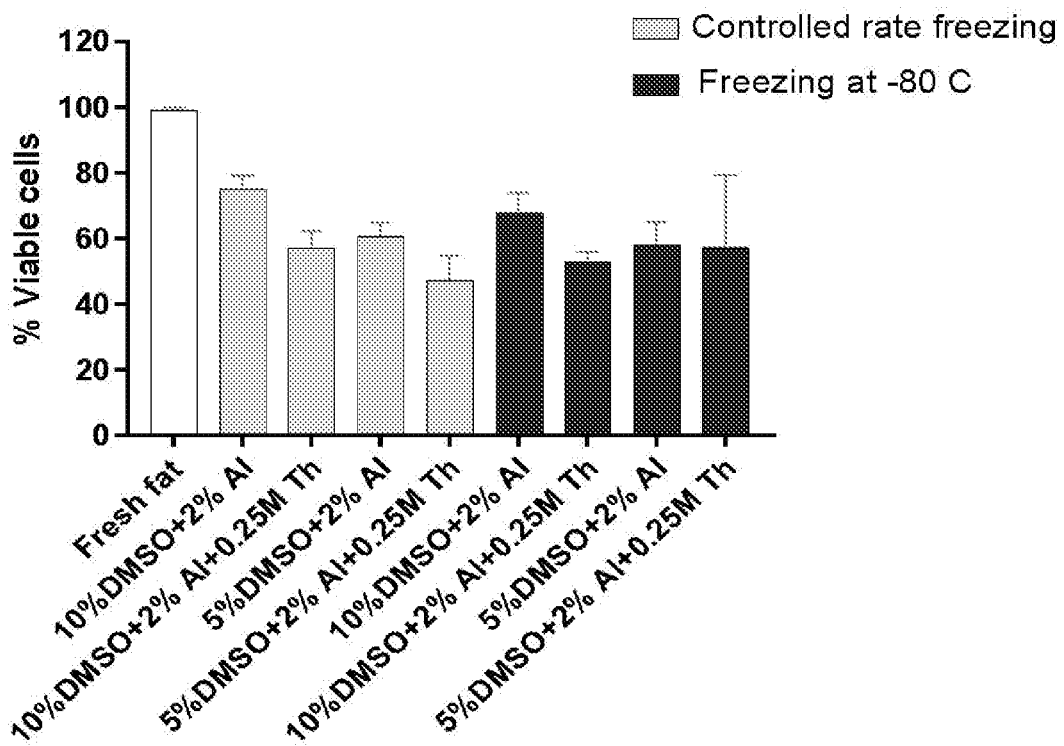
Figure 5A:
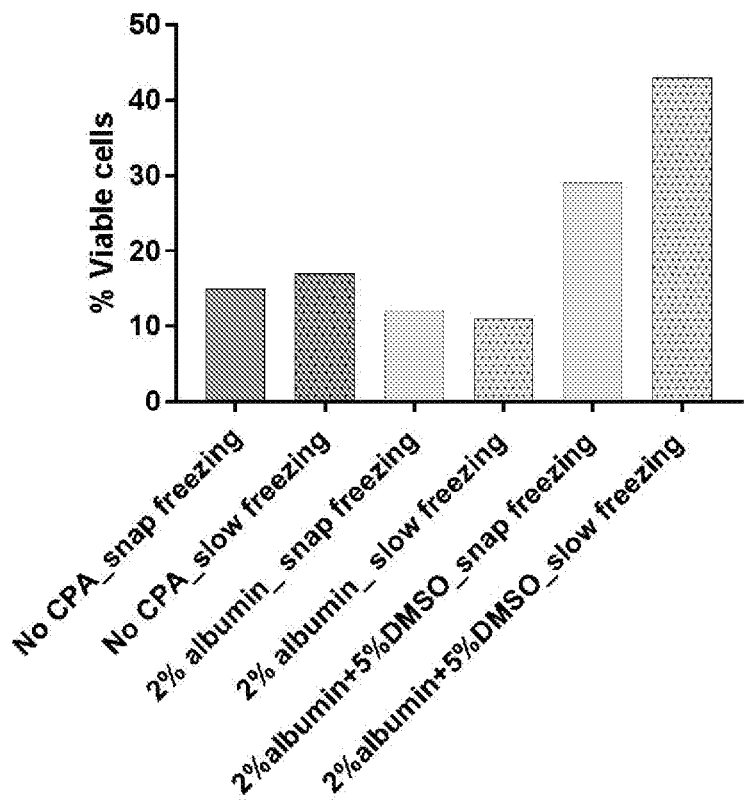
FIGS. 5A and 5B show results of analysis of ASCs (FIG. 5A) and adipocytes (FIG. 5B) viability using trypan blue stain, as described in Example 4.
Figure 5B:
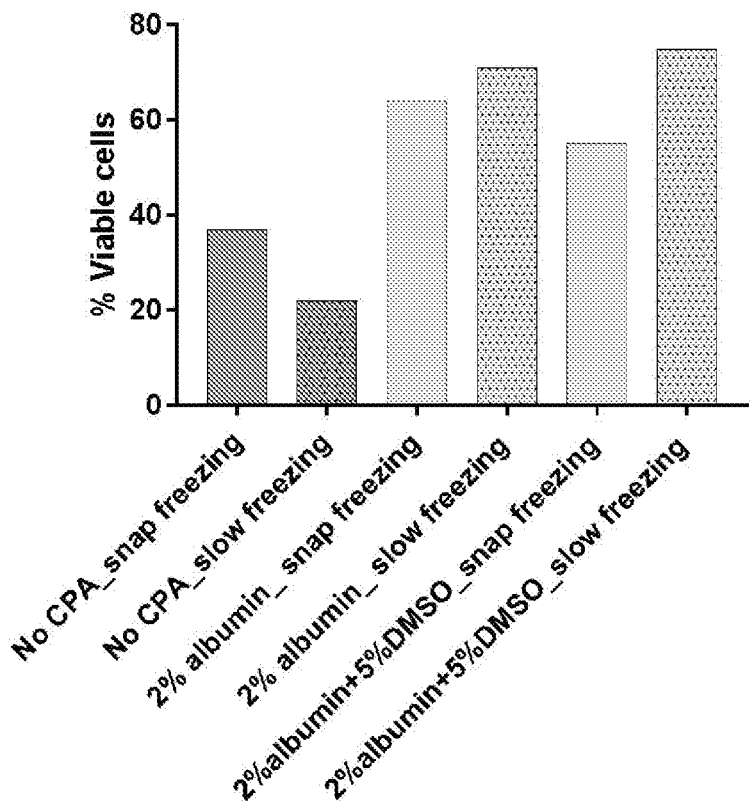

Methods: Lipo-aspirates were washed with PBS and liquid layer at the bottom and upper fat layer was removed. Equal quantity of lipo-aspirate (10 ml) was frozen under a controlled decrease in temperature or frozen at −80° C. in a Styrofoam box. Frozen aspirates were thawed after 48 hrs at 37° C. and washed with PBS. Following digestion with Collagenase, ASCs (FIG. 4A) and adipocytes (FIG. 4B) were analyzed for viability using trypan blue stain. Setting the % viable cells isolated from fresh fat as 100%, the percentage of viable cells following cryopreservation was calculated and plotted. Al=Albumin, Th=Trehalose Example 4 Cryopreservative Study Methods: Lipo-aspirates were washed with PBS and liquid layer at the bottom and upper fat layer was removed. Equal quantity of lipo-aspirate (7 ml) was either snap-frozen in liquid nitrogen or slow freezing was performed comprising, of 4 hrs at −20° C. and then at −80° C. in a cryobox to lower the temperature exchange. For both freezing conditions, the following Cryopreservation agent (CPA) settings were used: 1) without CPA; 2) 2% albumin; and 3) 2% albumin+5% DMSO. Frozen aspirates were thawed after 48 hrs at 37° C. and washed with PBS. Following digestion with Collagenase, ASCs (FIG. 5A) and adipocytes (FIG. 5B) were analyzed for viability using trypan blue stain.

The following numbered clauses describe various non-limiting aspects of the invention.

1. A cell or tissue isolation, purification, and storage device comprising: a vessel having a first end and a second end defining an internal chamber divided by a filter that retains fat cells or tissue and having a volume between the second end and the filter of at least 3 mL; a first adaptor or connector, such as a Luer lock or slip connector, at the first end of the vessel defining a first opening; and a second adaptor or connector, such as a Luer lock or slip connector, at the second end of the vessel and defining a second opening.

2. The device of clause 1, wherein the device is dimensioned to fit into a centrifuge able to centrifuge containers, e.g., tubes, bottles, syringes, or the device, having a volume within the range of from 1 mL to 4 L.

3. The device of clause 1 or 2, wherein the device is constructed to withstand centrifugation with a G-force of at least 500 g, e.g., at least 1000 g, 1200 g, or 1500 g.

4. The device of any one of clauses 1-3, wherein the internal chamber of the vessel has a volume ranging from 5 mL to 100 mL, e.g., 5 mL, 10 mL, 15 mL, 30 mL, or 50 mL.

5. The device of any one of clauses 1-4, dimensioned to fit into a centrifuge able to centrifuge containers, e.g., tubes, bottles, or syringes, having a volume within the range of from 1 mL to 4 L.

6. The device of any one of clauses 1-5, wherein the filter is closer to the second end of the vessel than the first end of the vessel.

7. The device of any one of clauses 1-6, wherein the vessel comprises two pieces separable pieces, forming the contiguous sealed vessel, the pieces being connected by a slip connector or a screw connector at a point closer to the first end of the vessel than the second end of the vessel, and optionally adjacent to the first end of the vessel.

8. The device of any one of clauses 1-7, wherein the filter is a 100 micron (μ) filter.

9. The device of any one of clauses 1-8, wherein the first adaptor and/or the second adapter are Luer lock adapters.

10. The device of any one of clauses 1-9, wherein the first adaptor and the second adapter are Luer lock adapters.

11. The device of any one of clauses 1-10, having a cylindrical cross-sectional profile.

12. The device of any one of clauses 1-11, having the diameter of a 10 mL medical syringe barrel.

13. The device of clause 12, the vessel having an outside diameter ranging from 16.5 to 18 mm, and a length ranging from 80 mm to 90 mm.

14. The device of any one of clauses 1-11, wherein the internal volume of the vessel between the filter and the first end of the vessel is 5 mL or greater, e.g., ranges from 8 mL to 10 mL.

15. The device of any one of clauses 1-11, the vessel having an outside diameter ranging from 5 mm to 25 mm, and a length ranging from 70 mm to 110 mm.

16. The device of any one of clauses 1-15, the vessel having a ratio of the length of the barrel to the outside diameter of the barrel is at least 4:1, or from 4:1 to 6:1.
17. The device of any one of clauses 1-16, comprising live cells, such as live fat cells, and, optionally, cryoprotectant, in the internal chamber of the vessel between the first end of the vessel and the filter.
18. A kit for use in isolating and storing cells, such as a fat graft, comprising:
    from two to 25 cell or tissue storage devices, each storage device comprising a vessel having a first end and a second end defining an internal chamber divided by a filter that retains fat cells or tissue and having a volume between the second end and the filter of at least 3 mL; a first adaptor or connector, such as a Luer lock or slip connector, at the first end of the vessel defining a first opening; and a second adaptor or connector, such as a Luer lock or slip connector, at the second end of the vessel and defining a second opening; and
    at least one vessel, optionally having an adaptor or connector, such as a Luer lock or slip connector, comprising an amount of cryoprotectant able to cryopreserve at least 3 mL of cells or tissue, such as an adipose graft.
19. The kit of clause 18, wherein the device is dimensioned to fit into a centrifuge able to centrifuge containers, e.g., tubes, bottles, syringes, or the device, having a volume within the range of from 1 mL to 4 L.
20. The kit of clause 18 or 19, wherein the device is constructed to withstand centrifugation with a G-force of at least 500 g, e.g., at least 1000 g, 1200 g, or 1500 g.
21. The kit of any one of clauses 18-20, wherein the internal chamber of the vessel has a volume ranging from 5 mL to 100 mL, e.g., 5 mL, 10 mL, 15 mL, 30 mL, or 50 mL.
22. The device of any one of clauses 18-21, dimensioned to fit into a centrifuge containers, e.g., tubes, bottles, or syringes, having a volume within the range of from 1 mL to 4 L.
23. The kit of any one of clauses 18-22, further comprising a storage container configured to store the two to 25 cell or tissue storage devices, optionally including labels for labeling the storage vessels and/or the storage container.
24. The kit of any one of clauses 18-23, further comprising a temperature logger (temperature recorder), optionally attached to the storage container.
25. The kit of any one of clauses 18-24, wherein the filter is closer to the second end of the vessel than the first end of one or more, or all, of the two to 25 vessels.
26. The kit of any one of clauses 18-25, wherein one or more, or all, of the two to 25 vessels comprises two pieces separable pieces, forming the contiguous sealed vessel, the pieces being connected by a slip connector or a screw connector at a point closer to the first end of the vessel than the second end of the vessel, and optionally adjacent to the first end of the vessel.
27. The kit of any one of clauses 18-26, wherein the filter of one or more, or all, of the two to 25 vessels is a 100 micron (μ) filter.
28. The kit of any one of clauses 18-27, wherein the first adaptor and/or the second adapter of one or more, or all, of the two to 25 vessels are Luer lock adapters.
29. The kit of any one of clauses 18-27, wherein the first adaptor and the second adapter of one or more, or all, of the two to 25 vessels are Luer lock adapters.
30. The kit of any one of clauses 18-29, wherein one of more, or all, of the two to 25 vessels has a cylindrical cross-sectional profile.
31. The kit of any one of clauses 18-30, wherein one of more, or all, of the two to 25 vessels has a diameter of a 10 mL medical syringe barrel.
32. The kit of any one of clauses 18-31, wherein the internal volume of one of more, or all, of the two to 25 vessels between the filter and the first end of the vessel is 5 mL or greater, e.g., ranges from 8 mL to 10 mL.
33. The kit of any one of clauses 18-31, wherein one of more, or all, of the two to 25 vessels has an outside diameter ranging from 5 mm to 25 mm, and a length ranging from 70 mm to 110 mm.
34. The kit of any one of clauses 18-31, wherein one of more, or all, of the two to 25 vessels has an outside diameter ranging from 16.5 to 18 mm, and a length ranging from 80 mm to 90 mm.
35. The kit of any one of clauses 18-31, wherein one of more, or all, of the two to 25 vessels has a ratio of the length of the barrel to the outside diameter of the barrel is at least 4:1, or from 4:1 to 6:1.
36. The kit of any one of clauses 18-35, wherein the cryoprotectant comprises dimethyl sulfoxide (DMSO), human serum albumin, trehalose, or a combination of two or more of any of the preceding, such as DMSO with hSA, e.g., 5%-10% (v/v) DMSO and 2% (w/v) hSA.
37. A method of preparing a fat graft comprising: introducing (e.g., injecting) fat tissue into the internal chamber of the device according to any one of clauses 1-16 through the second opening of the device; introducing an amount of a cryoprotectant effective to cryopreserve the fat graft into the internal chamber of the device through the first opening of the device; mixing the fat tissue with the cryoprotectant; and cooling the fat graft to a temperature below 0° C.
38. The method of clause 37, wherein the device is dimensioned to fit into a centrifuge able to centrifuge containers, e.g., tubes, bottles, syringes, or the device, having a volume within the range of from 1 mL to 4 L.
39. The method of clause 37 or 38, wherein the device is constructed to withstand centrifugation with a G-force of at least 500 g, e.g., at least 1000 g, 1200 g, or 1500 g.
40. The method of clause 37, further comprising after cooling the fat graft, raising the temperature of the fat graft to thaw the fat graft.
41. The method of any one of clauses 37-40, wherein the temperature of the fat graft during freezing or thawing is changed no more than 2° C. per minute, or no more than 1° C. per minute.
42. The method of any one of clauses 37-41, further comprising separating the fat graft from the cryoprotectant; drawing the cryoprotectant from the first end of the device; and washing the fat graft by: introducing an amount of wash solution into the first end of the device effective to wash the fat graft, mixing the wash solution with the fat graft; separating the fat graft from the wash solution; and drawing the wash solution from the first end of the device.
43. The method of any one of clauses 37-41, further comprising, centrifuging the device containing the thawed fat graft with the first opening on the bottom to separate the fat graft from the cryoprotectant; drawing the cryoprotectant from the first end of the device; and washing the fat graft by: introducing an amount of wash solution into the first end of the device effective to wash the fat graft, mixing the wash solution with the fat graft; centrifuging the device containing the fat graft with the first opening on the bottom, to separate the fat graft from the wash solution; and drawing the wash solution from the first end of the device.

44. The method of clause 42 or 43, wherein the fat graft is washed from two to six times.
45. The method of any one of clauses 42-44, wherein the wash solution is phosphate-buffered saline or saline (e.g. 0.9% w/v normal saline).
46. The method of any one of clauses 37-45, wherein the cryoprotectant comprises dimethyl sulfoxide (DMSO, human serum albumin (hSA), trehalose, or a combination of any of the preceding, such as DMSO with hSA, e.g., 5%-10% (v/v) DMSO and 2% (w/v) hSA.
47. A method of preparing a fat graft comprising: introducing (e.g., injecting) fat tissue into the internal chamber of the device according to any one of clauses 1-15 through the second opening of the device; introducing an amount of a wash solution effective to wash the fat graft into the internal chamber of the device through the first opening of the device; mixing the fat tissue with the wash solution; centrifuging the device containing the fat graft with the first opening on the bottom, to separate the fat graft from the wash solution; and drawing the wash solution from the first end of the device.
48. A method of preparing a fat graft comprising: introducing (e.g., injecting) fat tissue into the internal chamber of the device according to any one of clauses 1-15 through the second opening of the device; introducing an amount of a wash solution effective to wash the fat graft or an amount of a cryoprotectant effective to cryopreserve the fat graft into the internal chamber of the device through the first opening of the device; and mixing the fat tissue with the wash solution or the cryoprotectant; and either: when wash solution is introduced, centrifuging the device containing the fat graft with the first opening on the bottom, to separate the fat graft from the wash solution; and drawing the wash solution from the first end of the device, or when cryoprotectant is introduced, cooling the fat graft to a temperature below 0° C.
49. The method of clause 48, wherein wash solution is introduced into the device after the fat graft is introduced into the device; the wash solution and the fat graft are mixed; the device containing the fat graft is centrifuged with the first opening on the bottom, to separate the fat graft from the wash solution; and the wash solution is drawn from the first end of the device.
50. The method of clause 48, wherein the cryoprotectant is introduced into the device after the fat graft is introduced into the device; the cryoprotectant and fat graft are mixed, and the fat graft is cooled to a temperature below 0° C.

The embodiments have been described with reference to various examples. Modifications and alterations will occur to others upon reading and understanding the foregoing examples. Accordingly, the foregoing examples are not to be construed as limiting the disclosure.

What is claimed is:

1. A kit for use in isolating and storing cells, comprising:
   from two to 25 cell or tissue storage devices, each storage device comprising
   at least one individual patient label on each storage device comprising an indicia relating to an individual patient;
   a vessel having a first end and a second end defining an internal chamber configured to retain fat cells or tissue, the vessel comprising two separable pieces forming a contiguous sealed vessel with a continuous annular outer surface formed by the two separable pieces dimensioned to fit into a centrifuge configured to centrifuge containers, the two separable pieces being connected by a fitting portion positioned closer to the first end of the vessel than to the second end of the vessel;
   a first adaptor at the first end of the vessel comprising a slip Luer connector or a threaded Luer connector defining a first opening extending through the first adaptor to the internal chamber of the vessel; and
   a second adaptor at the second end of the vessel comprising a slip Luer connector or a threaded Luer connector and defining a second opening extending through the second adaptor to the internal chamber of the vessel;
   a container comprising an interior, an exterior surface, and inserts disposed in the interior of the container configured to receive the from two to 25 cell or tissue storage devices; and
   an external label positioned on the exterior surface of the container comprising indicia for each individual patient identified on the at least one individual patient labels of the from two to 25 cell or tissue storage devices and an indicia for a storage date of fat grafts contained in the from two to 25 cell or tissue storage devices,
   wherein the two separable pieces of the vessel of the from two to 25 cell or tissue storage devices comprise:
   a first piece comprising a first barrel portion comprising an end that is connected to or integral with the first adaptor, an opposing end, a sidewall having an inner surface extending between the ends of the first barrel portion, and the fitting portion extending from the opposing end of the first barrel portion, wherein an inner diameter of the first opening of the first adaptor is less than an inner diameter of the first barrel portion; and
   a second piece comprising a second barrel portion comprising an end that is connected to or integral with the second adaptor, an opposing end, and a sidewall having an inner surface extending between the ends of the second barrel portion, wherein an inner diameter of the second opening of the second adaptor is less than an inner diameter of the second barrel portion,
   wherein the fitting portion of the first piece is directly inserted into the second barrel portion of the second piece and engages the inner surface of the second barrel portion, thereby forming the contiguous sealed vessel having the internal chamber which is defined by the inner surfaces of the first barrel portion and the second barrel portion,
   wherein the slip Luer connector or the threaded Luer connector of the first adapter or the second adapter is configured to engage a corresponding slip or threaded Luer connector of a medical syringe, and wherein the vessel of at least one of the from two to 25 cell or tissue storage devices comprises an amount of cryoprotectant, able to cryopreserve at least 3 mL of cells or tissue.

2. The kit of claim 1, wherein the internal chamber of each storage device has a volume within the range of from 1 mL to 4 L and the device is constructed to withstand centrifugation with a G-force of at least 500 g.

3. The kit of claim 1, comprising live cells and, optionally, cryoprotectant, in the internal chamber of the vessel of one or more of the from two to 25 cell or tissue storage devices.

4. The kit of claim 1, wherein the from two to 25 cell or tissue storage devices are dimensioned to fit into a centrifuge able to centrifuge containers having a volume within the range of from 1 mL to 4 L, and the device is constructed to withstand centrifugation with a G-force of at least 500 g.

5. The kit of claim 1, further comprising a temperature logger.

6. The kit of claim 1,
wherein the two separable pieces of one or more, or all, of the two to 25 vessels have an outside diameter ranging from 16.5 to 18 mm, and a total length of the one or more, or all, of the two to 25 vessels ranges from 80 mm to 90 mm.

7. The kit of claim 1, wherein one or more, or all, of the two to 25 vessels further comprise a filter disposed in the second barrel portion having a diameter matching the inner diameter of the second barrel portion and that retains the fat cells or tissue between the first end of the vessel and the filter,
wherein a space enclosed by the second end of the vessel, the filter, and the inner surface of the sidewall of the second barrel portion has a volume of at least 3 mL, and
wherein the filter is closer to the second end of the vessel than the first end of the vessel.

8. The kit of claim 1, wherein, the from two to 25 cell or tissue storage devices are configured such that when the first piece is connected to the second piece, an annular outer surface of the first barrel portion of the first piece is flush with an annular outer surface of the second barrel portion of the second piece, and wherein an outside diameter of each of the first piece and the second piece is from 16.5 mm to 18 mm.

9. The kit of claim 1, wherein the fitting portion of the from two to 25 cell or tissue storage devices comprises a tube comprising an open first end integral with the open end of the first barrel portion, an open second end opposite the first end, and a sidewall extending therebetween.

10. The kit of claim 9, wherein an outer diameter of the first barrel portion of the from two to 25 cell or tissue storage devices is equal to an outer diameter of the second barrel portion of the from two to 25 cell or tissue storage devices, and wherein an outer diameter of the fitting portion is equal to an inner diameter of the second barrel portion.

11. A method of storing tissue or cells, the method comprising introducing the tissue or cells into the internal chamber of at least one device of the from two to 25 cell or tissue storage devices of the kit of claim 1 through the second opening of the at least one device;
attaching the at least one individual patient label on the at least one device;
positioning the at least one device in the interior of the container of the kit; and
attaching the external label to the exterior surface of the container.

12. A method of preparing a fat graft comprising: introducing fat tissue into the internal chamber of at least one device of the from two to 25 cell or tissue storage devices of the kit of claim 1 through the second opening of the at least one device; introducing an amount of a wash solution effective to wash the fat graft or an amount of a cryoprotectant effective to cryopreserve the fat graft into the internal chamber of the at least one device through the first opening of the at least one device; and mixing the fat tissue with the wash solution or the cryoprotectant; and either: when wash solution is introduced, centrifuging the at least one device containing the fat graft with the first opening on the bottom, to separate the fat graft from the wash solution; and drawing the wash solution from the first end of the device, or when cryoprotectant is introduced, cooling the fat graft to a temperature below 0° C.

13. The method of claim 12, wherein wash solution is introduced into the at least one device after the fat graft is introduced into the at least one device; the wash solution and the fat graft are mixed; the fat graft is separated from the wash solution; and the wash solution is drawn from the first end of the at least one device.

14. The method of claim 12, wherein cryoprotectant is introduced into the at least one device after the fat graft is introduced into the device; the cryoprotectant and fat graft are mixed, and the fat graft is cooled to a temperature below 0° C.

15. A method for adipose tissue storage and isolation within at least one device of the from two to 25 cell or tissue storage devices of the kit of claim 1, the method comprising:
drawing adipose tissue into the internal chamber of the vessel of at least one device of the from two to 25 cell or tissue storage devices through the first adaptor or connector of the at least one device;
introducing an amount of a cryoprotectant effective to cryopreserve the adipose tissue into the internal chamber of the vessel through the second adaptor or connector of the at least one device;
mixing the adipose tissue with the cryoprotectant; and
cooling the adipose tissue to a temperature below 0° C.

16. The method of claim 15, further comprising:
after cooling the adipose tissue, thawing the adipose tissue by raising the temperature of the adipose tissue;
centrifuging the device containing the thawed adipose tissue to separate the adipose tissue from the cryoprotectant;
drawing the cryoprotectant from the internal chamber of the vessel through a filter disposed in the second barrel portion and through the second adapter or connector of the device; and
washing the adipose tissue by:
introducing an amount of wash solution through the second adaptor or connector of the device effective to wash the adipose tissue,
mixing the wash solution with the adipose tissue in the internal chamber of the vessel;
centrifuging the device containing the adipose tissue to separate the adipose tissue from the wash solution; and
drawing the wash solution through the filter disposed in the second barrel portion and through the second adaptor or connector of the device.

* * * * *